(12) United States Patent
Szente et al.

(10) Patent No.: US 11,446,325 B2
(45) Date of Patent: Sep. 20, 2022

(54) CYCLODEXTRIN DERIVATIVES IN THE TREATMENT OR PREVENTION OF LYSOSOMAL NEURODEGENERATIVE DISEASES

(71) Applicant: CYCLOLAB CYCLODEXTRIN RESEARCH AND DEVELOPMENT LABORATORY LTD., Budapest (HU)

(72) Inventors: Lajos Szente, Budapest (HU); István Puskas, Budapest (HU); Tamas Sohajda, Halásztelek (HU)

(73) Assignee: CYCLOLAB CYCLODEXTRIN RESEARCH AND DEVELOPMENT LABORATORY LTD., Budapest (HU)

( * ) Notice: Subject to any disclaimer, the term of this patent is extended or adjusted under 35 U.S.C. 154(b) by 163 days.

(21) Appl. No.: 17/039,483

(22) Filed: Sep. 30, 2020

(65) Prior Publication Data
US 2022/0096528 A1 Mar. 31, 2022

(51) Int. Cl.
A61K 31/724 (2006.01)
A61P 25/28 (2006.01)

(52) U.S. Cl.
CPC ............ *A61K 31/724* (2013.01); *A61P 25/28* (2018.01)

(58) Field of Classification Search
CPC ........... A61K 31/724; A61P 25/28; A61P 3/06
See application file for complete search history.

(56) References Cited

U.S. PATENT DOCUMENTS

RE44,733 E * 1/2014 Zhang ..................... A61P 21/00
514/231.5
2016/0361344 A1 * 12/2016 Salome ..................... A61P 9/00
2018/0371110 A1  12/2018 Kennedy et al.

FOREIGN PATENT DOCUMENTS

| EP | 3 078 379 A1 | 10/2016 |
| WO | WO 2016/201137 A1 | 12/2016 |
| WO | WO 2019/067269 A2 | 4/2019 |
| WO | WO 2020/018498 A1 | 1/2020 |

OTHER PUBLICATIONS

Bom et al., "Preclinical pharmacology of sugammadex". Journal of Critical Care (2009) 24, pp. 29-35.
Booij et al., "In vivo animal studies with sugammadex", Anaesthesia, 2009, 64 (Suppl. 1), pp. 38-44.
Chen et al., "Cyclodextrin Induces Calcium-Dependent Lysosomal Exocytosis", PLoS ONE, Nov. 2010, vol. 5, Issue 11, e15054, pp. 1-7.
Coisne et al., "Cyclodextrins as Emerging Therapeutic Tools in the Treatment of Cholesterol-Associated Vascular and Neurodegenerative Diseases", Molecules 2016, 21, 1748, pp. 1-22.
Crumling et al., "Hearing Loss and Hair Cell Death in Mice Given the Cholesterol-Chelating Agent Hydroxypropyl-β-Cyclodextrin", PLOS ONE, Dec. 2012, vol. 7, Issue 12, e53280, pp. 1-8.
Davidson et al., "Chronic Cyclodextrin Treatment of Murine Niemann-Pick C Disease Ameliorates Neuronal Cholesterol and Glycosphingolipid Storage and Disease Progression", PLoS ONE, Sep. 2009, vol. 4, Issue 9, e6951, pp. 1-15.
Davidson et al., "Efficacy and ototoxicity of different cyclodextrins in Niemann-Pick C disease", Annals of Clinical and Translational Neurology, Open Access, American Neurological Association, 2016, pp. 1-15.
Della Rocca et al., "A novel approach to reversal of neuromuscular blockade", Minerva Anestesiologica, 2009, vol. 75, No. 5, pp. 349-351.
Egele et al., "Synthesis of the Anionic Hydroxypropyl-β-cyclodextrin:Poly(decamethylenephosphate) Polyrotaxane and Evaluation of its Cholesterol Efflux Potential in Niemann-Pick C1 Cells", J Mater Chern B., Jan. 28, 2019, 7(4), pp. 528-537.
Infante et al., "NPC2 facilitates bidirectional transfer of cholesterol between NPC1 and lipid bilayers, a step in cholesterol egress from lysosomes", PNAS, Oct. 7, 2008, vol. 105, No. 40, pp. 15287-15292.
Kulkarni et al., "Linear Cyclodextrin Polymer Prodrugs as Novel Therapeutics for Niemann-Pick Type C1 Disorder", Scientific Reports, Accepted Jun. 13, 2018, Published online Jun. 22, 2018, total of 13 pages.
Liu et al., "Cyclodextrin overcomes the transport defect in nearly every organ of NPC1 mice leading to excretion of sequestered cholesterol as bile acid", Journal of Lipid Research, vol. 51, 2010, pp. 933-944.
Liu et al., "Genetic variations and treatments that affect the lifespan of the NPC1 mouse", Journal of Lipid Research, vol. 49, 2008, pp. 663-669.
Liu et al., "Reversal of defective lysosomal transport in NPC disease ameliorates liver dysfunction and neurodegeneration in the npc1$^{-/-}$ mouse", PNAS, Feb. 17, 2009, vol. 106, No. 7, pp. 2377-2382.
Ramirez et al., "Quantitative role of LAL, NPC2, and NPC1 in lysosomal cholesterol processing defined by genetic and pharmacological manipulations", Journal of Lipid Research, vol. 52, 2011, pp. 688-698.
Rosenbaum et al., "Niemann-Pick type C disease: molecular mechanisms and potential therapeutic approaches", NIH Public Access, Author Manuscript, J Neurochem., Mar. 2011; 116(5): 789-795, pp. 1-11.
Vanier, "Complex lipid trafficking in Niemann-Pick disease type C", J Inherit Metab Dis, Complex Lipids, Revised Oct. 31, 2014, Accepted Nov. 9, 2014, Published online Nov. 26, 2014, total of 13 pages.

(Continued)

*Primary Examiner* — Leigh C Maier
(74) *Attorney, Agent, or Firm* — Birch, Stewart, Kolasch & Birch, LLP

(57) ABSTRACT

The present invention generally relates to use of single isomer chemically modified cyclodextrins, namely, S-(carboxyalkyl)-thio-cyclodextrin salts in medication used for the prevention or treatment of lysosomal storage diseases.
More particularly, the present invention relates to isomer-pure, single isomer hexakis-S-(carboxyalkyl)-hexathio-alpha-cyclodextrin sodium salts, heptakis-S-(carboxyalkyl)-heptathio-beta-cyclodextrin sodium salts and octakis-S-(carboxyalkyl)-octathio-gamma-cyclodextrin sodium salts in medication used for the prevention or treatment of lysosomal storage diseases.

4 Claims, 1 Drawing Sheet

(56) References Cited

OTHER PUBLICATIONS

Ward et al., "2-Hydroxypropyl-β-Cyclodextrin Raises Hearing Threshold in Normal Cats and in Cats With Niemann-Pick Type C Disease", Pediatric Research, vol. 68, No. 1, 2010, pp. 52-56.
International Search Report and Written Opinion of the International Searchina Authority (Forms PCT/ISA/220, PCT/ISA/210 and PCT/ISA/237) for Internationa Application No. PCT/IB2021/058935, dated Dec. 20, 2021.

* cited by examiner

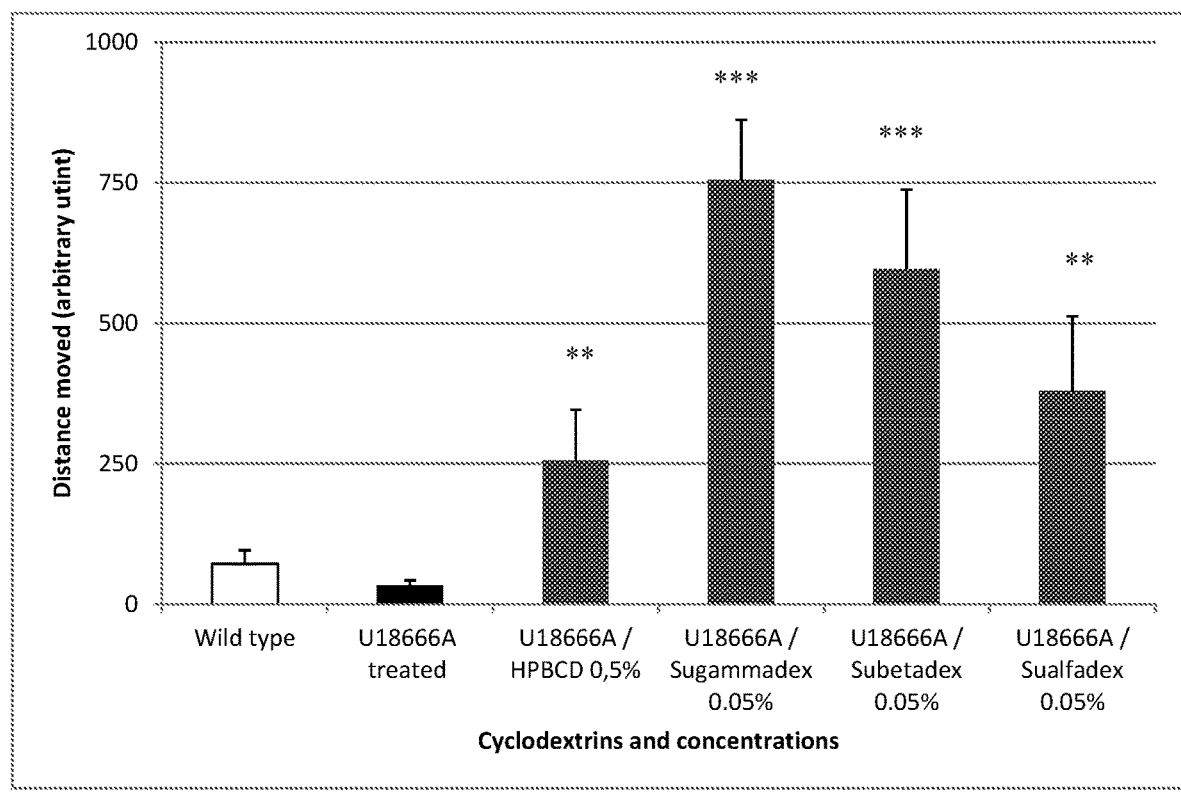

CYCLODEXTRIN DERIVATIVES IN THE TREATMENT OR PREVENTION OF LYSOSOMAL NEURODEGENERATIVE DISEASES

FIELD OF THE INVENTION

The present invention generally relates to the use of single isomer chemically modified cyclodextrins, namely, S-(carboxyalkyl)-thio-cyclodextrin salts in medication used for the prevention or treatment of lysosomal storage diseases.

More particularly, the present invention relates to isomer-pure, single isomer hexakis-S-(carboxyalkyl)-hexathio-alpha-cyclodextrin sodium salts, heptakis-S-(carboxyalkyl)-heptathio-beta-cyclodextrin sodium salts and octakis-S-(carboxyalkyl)-octathio-gamma-cyclodextrin sodium salts in medication used for the prevention or treatment of lysosomal storage diseases.

BACKGROUND OF THE INVENTION

Lysosomal storage disease (LSD) is a term for about fifty rare inherited metabolic disorders that result from defects in lysosomal function. Lysosomes are organellae of enzymes within cells that digest large molecules and pass the fragments on to other parts of the cell for recycling. This process requires several enzymes. If one of these enzymes is defective, (e.g because of a mutation), the large molecules accumulate within the cell, eventually making it dysfunctional. Lysosomal storage disorders are caused by lysosomal malfunction usually as a consequence of deficiency of a single enzyme required for the metabolism of lipids.

U18666A, an intra-cellular cholesterol transport inhibitor, due to its multiple actions have enabled major discoveries in lipid research and contributed to understanding the pathophysiology of multiple diseases including LSDs. U18666A inhibits oxidosqualene cyclase leading to discover pathways for formation of polar sterols that he proved to be important regulators of lipid metabolism. It was recognized that U18666A inhibits the egress of cholesterol from late endosomes and lysosomes leading to greatly improved perspective on the major pathways of intracellular cholesterol trafficking. The inhibition of cholesterol trafficking by U18666A mimicks the loss of functional proteins responsible for LSD diseases and thus provides a model for these disorders. U18666A subsequently became a tool for assessing the importance of molecular trafficking through the lysosomal pathways in several disease conditions such as atherosclerosis, Alzheimer's disease, and prion infections. U18666A also provides animal models for two important disorders: petite mal (absence) epilepsy and cataracts. Use of this compound was the first chronic model of absence epilepsy. U18666A is also being used to address the role of oxidative stress in apoptosis. Consequently, the pathological model condition triggered by the application of U18666A may provide a tool for testing various possible therapeutical strategies.

Cyclodextrins (CDs) are a group of cyclic oligosaccharides that are obtained from the enzymatic transformation of starch by the action of the enzyme CD glycosyltransferase elaborated by e.g. bacterium *Bacillus macerans*. CDs form host-guest complexes with a wide range of compounds and are commonly used as excipients. These enzyme-modified starch derivatives are cyclic oligosaccharides toroid in shape with a hydrophobic inner cavity and hydrophilic exterior. There are three unmodified ("parent") types, alpha-, beta-, and gamma-CDs, composed of 6, 7, and 8 glucose units with increasing inner cavity diameter, respectively. Chemical derivatization of parent CDs is used to change solubility profiles, complexation properties, biodegradability, and toxicity.

The use of CDs for the treatment of cholesterol-associated neurodegenerative diseases was reviewed by Coisne et al. (Molecules 2016, 21, 1748). The utility of beta-CD, differently methylated beta-CDs, 2-hydroxypropyl beta cyclodextrin (HPBCD), per-6-alkylamino-beta-CD, sulfobutylether beta cyclodextrin are discussed. The article builds the concept of professional prejudice towards a single isomer gamma-CD derivative, called Sugammadex being unapplicable for such therapy: "beta-CDs have proven to be very useful in therapy as they have not shown any hypersensitivity reaction, unlike Sugammadex. This modified, single isomer gamma-CD used in anesthesia to reverse the effect of neurovascular blocking drugs has been involved in allergic response in some patients".

Patent application WO2019067269 describes (inter alia) a method of preventing or treating a lysosomal disease or disorder in a subject in need thereof comprising administering an effective amount of a CD to the subject. The specification does not provide teaching about the potential use of isomerically pure S-(carboxyalkyl)-thio-CDs, the disclosed potential therapeutic use is only demonstrated on the examples of native (unmodified) alpha-, beta-, gamma-CD, 2-hydroxypropyl alpha cyclodextrin, HPBCD and methyl beta cyclodextrin.

The most information related to the use of CDs for ameliorating LSD conditions is the application of cyclodextrins to treat Niemann-Pick type C (NPC) disease which is a multiorgan storage disorder characterized by lysosomal accumulation of unesterified cholesterol (UC) and other lipids. Central nervous system (CNS) neurons widely display polymembranous cytoplasmic storage bodies with intracellular accumulation of GM2 and GM3 gangliosides in addition to UC. Patients exhibit progressive neurological decline. Mutations of the NPC1 (~95% of patients) or NPC2 gene result in identical disease phenotype. (Vanier M T. Complex lipid trafficking in Niemann-Pick disease type C. J Inherit Metab Dis 2015; 38:187-199.). The two encoded proteins, transmembrane NPC1 and soluble luminal NPC2, are thought to interact with UC and/or other lipids in a coordinated fashion to facilitate their egress from late endosomal/lysosomal (LE/LY) compartments (Infante R E, Wang M L, Radhakrishnan A, et al. NPC2 facilitates bidirectional transfer of cholesterol between NPC1 and lipid bilayers, a step in cholesterol egress from lysosomes. Proc Natl Acad Sci USA 2008; 105:15287-15292.). Therapeutic strategies for NPC disease have included pharmacologic inhibition of substrate accumulation, increasing functionality of defective proteins, and targeting downstream sequelae such as inflammation and oxidative stress (Rosenbaum A I, Maxfield F R. Niemann-Pick type C disease: molecular mechanisms and potential therapeutic approaches. J Neurochem 2011; 116: 789-795.). The most efficacious therapy to date has been HPBCD which, following even subcutaneous administration to NPC1- or NPC2-deficient mice, delays clinical onset, extends lifespan, and reduces UC and glycolipid accumulation within the CNS and other organs (Davidson C D, et al. PLoS ONE 2009; 4:e6951.; Liu B, et al. J Lipid Res 2008; 3:663-669.; Liu B, et al. Proc Natl Acad Sci USA 2009; 106:2377-2382.; Liu B, et al. J Lipid Res 2010; 51:933-944.).

Several mechanisms by which therapeutic correction of Niemann-Pick type C disease is achieved by CDs have been proposed, but the predominant view is that CDs directly replace the function of NPC proteins within LE/LY compartments (Chen F W, et al. PLoS ONE 2010; 5:e15054, Ramirez C M, et al. J Lipid Res 2011; 52:688-698.). Supporting this idea, HPBCD treatment was also proved efficacious in mice deficient in both NPC proteins, but not in other diseases with functional NPC proteins and secondary lysosomal storage of cholesterol. Exactly how CD acts to emulate NPC protein function or otherwise mediate CNS correction remains unclear. Nearly, all therapy-related studies on NPC animal models have used HPBCD, a multicomposite, statistically derivatized beta-CD with hydroxypropyl side groups, yet little attention have been paid on how different possible chemically derivatized CDs might affect efficacy. Moreover, the potential efficaciousness of any other CD has been rarely investigated and since studies show that HPBCD is ototoxic (Ward S et al. Pediatr Res 2010; 68:52-56, Crumling M A et al. PLoS ONE 2012; 7:e53280.) identification of safer and more effective alternate CDs is greatly needed (e.g higher therapeutic effect of subject matter compounds was demonstrated even in one tenth reduced concentration compared to that of HPBCD as shown in Example 1 per present invention). One of the most probable reason of the high doses of currently used CD-derivatives (being all composite isomer mixtures) because of the composite nature of these CD-derivatives the indeed effective component(s) are not known and are diluted by close isomeric congeners of the CD-derivatives. The utility of single isomer CD-derivatives offers the possibility of achieve desired efficacy by applying lower doses. A screening study involving methyl-beta-CD, 2-hydroxypropyl alpha-, beta- and gamma-CD, sulfobutylether alpha-, beta- and gamma-CD showed that CDs other than HPBCD may provide disease amelioration without ototoxicity and merit long-term treatment studies wherein especially 2-hydroxypropyl gamma-CD and sulfobutylether gamma-CD were found effective in mouse NPC1 model (Davidson, C. D. et al. Annals of Clinical and Translational Neurology Volume 3, Issue 5, pages 366-380, 2016).

A therapeutic amount of intravenously administered HPBCD meeting United States Pharmacopoeia criteria (Trappsol® Cyclo™—CTD Inc.) is studied in a Phase III clinical trial dosed at 1500-2500 mg/body weight kg. HPBCD is in an orphan drug status in the European Union and United States. All these commercial currently administered HPBCD derivatives are complicated isomeric mixtures, highly composite materials consisting of thousands of positional, geometric and even optical isomeric species.

Vtesse, Inc. patented a HPBCD composition of narrower substitution distribution profile isolated from commercial compendial HPBCD wherein the starting material commercial HPBCD meets European Pharmacopoeia and United States Pharmacopoeia requirements (WO2016201137). The claimed product is a mixture of beta-cyclodextrin molecules substituted at one or more hydroxyl positions by hydroxypropyl groups. The mixture might include unsubstituted beta-cyclodextrin molecules, wherein the mixture comprises less than 1% unsubstituted beta-cyclodextrin ("DS-0") and beta-cyclodextrin substituted with one hydroxypropyl group ("DS-1"), collectively; the mixture comprises at least 85% beta-cyclodextrin substituted with three hydroxypropyl groups ("DS-3"), beta-cyclodextrin substituted with four hydroxypropyl groups ("DS-4"), beta-cyclodextrin substituted with five hydroxypropyl groups ("DS-5"), and beta-cyclodextrin substituted with six hydroxypropyl groups ('DS-6"), collectively; the mixture comprises less than 1% beta-cyclodextrin substituted with nine hydroxypropyl groups ("DS-9") and beta-cyclodextrin substituted with ten hydroxypropyl groups ("DS-10"), collectively, as determined by peak heights of an electrospray MS spectrum. The inventors suggest the use of such specified narrower distribution HPBCD (Adrabetadex, VTS-270) containing pharmaceutical composition for treating Niemann-Pick disease Type C administering by intrathecal or intracerebroventricular administration. A phase 2/3 clinical trial for VTS-270 is being conducted involving individuals between 2 and 25 years of age who have been diagnosed with NPC1.

Apart from HPBCD, the following cyclodextrin derivatives and complexes were evaluated for the treatment of NPC1 in preclinical studies:

Oraxion Therapeutics company has developed a beta-cyclodextrin based linear polymer of ~33 kDa molecular weight linked with biodegradable ketal-type of linker (ORX-301). It was demonstrated that subcutaneously injected ORX-301 extended the mean lifespan of NPC1 mice at a dosage 5-fold lower (800 mg/kg, body weight) the HPBCD dose proven efficacious (over 1500 mg/kg) (Kulkarni, A., et al. Sci Rep 8, 9547 (2018).) ORX-301 is in preclinical development.

Japan Maize Products Co Ltd, Nihon Shokuhin Kako Co Ltd and Kumamoto University NUC filed a patent application (EP3078379A1) for pharmaceutical composition for treating or preventing a lysosomal disease, comprising hydroxypropyl-gamma-cyclodextrin as an active ingredient.

To overcome a drawback of systemic HPBCD treatment, the rapid renal clearance of the therapeutic agent, Egele et al. designed an anionic HPBCD polyrotaxane to act as a slow release formulation based on a polyalkylene phosphate core to improve the pharmacokinetics (Egele et al. J Mater Chem B. 2019, 28; 7(4): 528-537). The polyalkylene phosphate comprises hydrophobic decamethylene spacers linked by biodegradable anionic phosphodiester bonds. HPBCD was threaded onto this polymer first and alpha-CD afterwards to prevent burst release of the threaded HPBCD. The findings showed that HPBCD was slowly released from the water soluble polyrotaxane. The polyrotaxane provided persistently diminished cholesterol levels in NPC1 cells by 20% relative to untreated ones.

BRIEF DESCRIPTION OF THE DRAWING

FIG. 1 shows Effects of the different treatments on locomotor activity of 5 day old zebrafish larvae. *$p<0.05$; $p<0.01$; *$p<0.001$

DETAILED DESCRIPTION

Present disclosure provides a more effective and safer composition alternative to statistically substituted, isomeric mixtures of different HPBCD species or HPBCD compositions currently applied to ameliorate lysosomal storage diseases. The drawback associated with the use of HPBCD composite is its high dose/exposure level (over 1500 mg/kg) and the known ototoxicity as side-effect related to its use. No wonder that this randomly substituted cyclodextrin derivative with complicated isomeric mixture was developed originally as excipient, and now used also as an active pharmaceutical ingredient, will exert untoward side effects, because it needs to be used in really high doses. Lysosomal storage disorders treated by the invention include, but are not limited to the following: Aspartylglucosaminuria, Wolman disease, Cystinosis, Danon disease, Fabry disease, Farber disease, Fucosidosis, Gaucher disease, GM1-Gangliosidosis types I/II/III, GM2-Gangliosidosis, alpha-Mannosidosis types I/II, beta-Mannosidosis, Metachromatic leukodystrophy, Sialidosis types I/II, Mucolipidosis type IV, Scheie syndrome, Hunter syndrome, Sanfilippo syndrome A, Sanfilippo syndrome B, Sanfilippo syndrome C, Sanfilippo syndrome D, Galactosialidosis types I/II, Krabbe disease, Sandhoff disease, Vogt-Spielmeyer disease, Hurler syndrome, Niemann-Pick disease Type C, I-cell disease (mucolipidosis II), pseudo-Hurler polydystrophy, Morquio syndrome, Maroteaux-Lamy syndrome, Sly syndrome, Mucopolysaccharidosis type IX, Multiple sulfatase deficiency, Batten disease, Tay-Sachs disease, Pompe disease, Batten disease, Batten disease, late infantile, Northern Epilepsy, Pycnodysostosis, Schindler disease, Sialuria, and Salla disease modellable by condition triggered by the use of U18666A.

We have surprisingly found that the following cyclodextrin derivative types are applicable for the purpose of ameliorating the above malignant conditions: S-(carboxyalkyl)-thio-cyclodextrin salts:

6A,6B,6C,6D,6E,7F-Hexakis-S-(2-carboxyethyl)-6A,6B,6C,6D,6E,6F-hexathio-alpha-cyclodextrin sodium (Sualfadex sodium)
  6A,6B,6C,6D,6E,7F,6G-Heptakis-S-(2-carboxyethyl)-6A,6B,6C,6D,6E,6F,6G-heptathio-beta-cyclodextrin sodium salt (Subetadex sodium)
  6A,6B,6C,6D,6E,7F,6G,6H-Octakis-S-(2-carboxyethyl)-6A,6B,6C,6D,6E,6F,6G,6H-octathio-gamma-cyclodextrin sodium salt (Sugammadex sodium)

In the light of previous findings in literature (L. Booij et al Anaesthesia 2009 March; 64 Suppl 1:38-44. and Anton Bom et al J Crit Care. 2009 March; 24 (1):29-35. and G Della Rocca et al Minerva Anestesiol. 2009 May; 75 (5): 349-51.) we surprisingly found that chemically pure, single isomer carboxyethyl-thio-cyclodextrins, originally designed as artificial receptors for the management of neuromuscular blockade, showed remarkable potency in the treatment of cholesterol and lipid storage disorders in animal models.

Example 1 shows the significant cholesterol-accumulation hindering activity of Sualfadex sodium, Subetadex sodium and Sugammadex sodium on a zebrafish (*Danio rerio*) LSD condition model in comparison with HPBCD as positive control. Example 2 shows that the LSD condition amelioration is manifested in improved motoric activity of the test animals due to the treatment with Sualfadex sodium, Subetadex sodium and Sugammadex sodium. Example 3 shows that the efficacy of the studied S-(carboxyalkyl)-thio-cyclodextrin salts are effective to ameliorate LSD conditions despite of their low cholesterol affinity compared to that of HPBCD which is a known medicament against a LSD disease.

EXAMPLE 1

Several cyclodextrin derivatives were evaluated in a zebrafish model for Niemann Pick type C1 (U18666A administration). Cholesterol accumulation in the brain was quantified by filipin staining of *Danio rerio* Casper (albino strain) larvae. Results were compared with the reference compound Hydroxypropyl-β-cyclodextrin (HPBCD).

In this study the best performing Cyclodextrins were as follows: Heptakis(2,6-di-O-methyl)-beta cyclodextrin, Octakis(2,3,6-tri-O-methyl)-gamma cyclodextrin, Sualfadex sodium, Subetadex sodium Sugammadex sodium. Filipin staining of five day old zebrafish larvae (*Danio rerio*, Casper strain) pretreated with U18666A were studied.

Fertilized eggs were hatched and kept in an incubator at 28° C.

CDs were administered from Stock solutions (0.1%) in standard E3 medium. Preparation of E3 medium was as follows:
Ingredients
34.8 g NaCl
1.6 g KCl
5.8 g $CaCl_2.2H_2O$
9.78 g $MgCl_2.6H_2O$ To prepare a 60× stock, the ingredients were dissolved in water, to a final volume of 2 L. pH was adjusted to 7.2 with NaOH, then autoclaved. To prepare 1× medium, 6.5 mL of the 60× stock was diluted to 1 L, then 100 μL of 1% methylene blue was added.

The stock solutions were diluted with E3. Compounds were administered in the swimming water. Each concentration was tested in 25 larvae. Dosing regimen is shown in Table 1.

TABLE 1

Dosing regimen of the treatments

| Group | Day 3 (17.00 h) | Day 4 (9.00 h) | Day 5 |
|---|---|---|---|
| U18666A - Placebo | E3 | E3 | Analysis |
| U18666A - Cyclodextrin | U18666A 0.25 ug/mL | Cyclodextrin | Analysis |

Experimental compounds were tested at a 0.05% concentration. As reference Hydroxypropyl-β-cyclodextrin (Sigma) was tested at a 0.5% concentration.

Filipin Staining

Treated 5 dpf Casper larvae were fixed for 30 minutes in 4% paraformaldehyde. After washing (2 times) with PBS, they were stained for 30 minutes with 50 μg/mL filipin (Sigma) in PBS solution. Then larvae were washed (with PBS) twice.

Whole larvae were embedded and images were captured on a Dino-Lite Digital USB microscope for GFP/FITC recordings (AM4115T4). Images were evaluated by an independent assessor, unaware of the treatments. The assessor scored the fluorescence in the head region as none, light or heavy.

Statistical Analyses

Data were analysed by means of X2-tests. All conditions were compared to the U18666A—placebo treatment group.

Effects on Filipin Staining

Fluorescence was measured as an index for the amount of filipin staining. The higher the filipin staining the more cholesterol accumulation there is in the brain. Individual larvae were scored (by a blinded assessor) as either heavy coloured, light coloured or not coloured at all. The number of larvae in each category is shown in Table 2.

TABLE 2

Filipin staining analysis of test groups.

| Compound | Dose tested | No staining | Light staining | Heavy staining | Different from placebo |
|---|---|---|---|---|---|
| U18666A + Placebo | — | 0 | 8 | 17 | |
| U18666A + HPBCD (reference) | 0.5% | 2 | 13 | 9 | * |
| U18666A + Heptakis(2,6-di-O-methyl)-beta cyclodextrin | 0.05% | 1 | 9 | 13 | |

TABLE 2-continued

Filipin staining analysis of test groups.

| Compound | Dose tested | No staining | Light staining | Heavy staining | Different from placebo |
|---|---|---|---|---|---|
| U18666A + Octakis(2,3,6-tri-O-methyl)-gamma cyclodextrin | 0.05% | 0 | 11 | 13 | |
| U18666A + Sualfadex sodium | 0.05% | 4 | 16 | 4 | *** |
| U18666A + Subetadex sodium | 0.05% | 4 | 15 | 5 | *** |
| U18666A + Sugammadex sodium | 0.05% | 5 | 15 | 4 | *** |

U18666A treated animals (U18666A—placebo) were mainly heavy colored (17 out of 25 animals) which showed that the compound induced cholesterol accumulation in the brain. This accumulation was significantly reduced by HPBCD (only 9 out of 24 animals showed heavy colouration and 2 larvae were not coloured at all). Heptakis(2,6-di-O-methyl)-beta cyclodextrin and Octakis(2,3,6-tri-O-methyl)-gamma cyclodextrin showed only a small, non-significant, reduction in U18666A induced cholesterol accumulation. Sualfadex sodium, Subetadex sodium and Sugammadex sodium (0.05%) were very active; these single isomer compounds induced a very strong reduction in the cholesterol accumulation. The compound was more active than the reference HPBCD (even though used at 10× concentration: 0.5%).

EXAMPLE 2

Mobility Testing

*Danio rerio* larvae (strain AB, Casper) 5 days post fertilization (dpf) at day of testing were treated with U18666A dissolved in standard E3 medium. Reversal of U18666A (1 microg/ml) effects on overall activity of 5 dpf *Danio rerio* larvae by different CDs at different concentrations (0.5-5%) were tested. Larvae were pretreated with U18666A for 16 hours and thereafter treated with CD for 24 hours. Statistical analyses were performed for the individual experiments with two way ANOVA's followed by Tukey post hoc tests (**$p<0.01$). CDs were dissolved in standard E3 medium.

Behaviour of the test species were observed in 48-wells plates in Danio Vision (Noldus IT, Wageningen). DanioVision Observation Chamber which is a complete system, designed for the high-throughput testing of zebrafish larvae in 48-wells plates. It includes an observation chamber and renowned EthoVision XT video tracking software to quantify distance moved by the animals. The results are graphically represented (distance moved—in arbitrary unit) in FIG. 1.

EXAMPLE 3

Interaction of Cyclodextrins with Unesterified Cholesterol

Phase solubility studies were performed in 5 ml solutions at room temperature, wherein cyclodextrin solutions of discrete concentrations were weighed and excess amount of cholesterol was added. After 24 hours equilibration time at 25±3° C. (using magnetic stirrer at 500 RPM), the dissolved equilibrium cholesterol concentrations were determined by HPLC after filtration through a syringe filter having polyethylene sulfone membrane of 0.45 micron nominal pore size. The experimentally determined cholesterol concentrations in the presence of different concentrations of HPBCD, Sualfadex sodium, Subetadex sodium and Sugammadex sodium are listed in Table 3.

TABLE 3

Equilibrium concentrations of cyclodextrin solubilized cholesterol

| CD concentration | Dissolved chlolesterol concentration (mg/ml) in HPBCD solutions | Dissolved chlolesterol concentration (mg/ml) in Sualfadex Na. solutions | Dissolved chlolesterol concentration (mg/ml) in Subetadex Na. solutions | Dissolved chlolesterol concentration (mg/ml) in Sugammadex Na. solutions |
|---|---|---|---|---|
| 0 w/w % | <0.01 | <0.01 | <0.01 | <0.01 |
| 5 w/w % | 0.28 | 0.016 | 0.062 | 0.056 |
| 10 w/w % | 0.98 | 0.028 | 0.092 | 0.062 |
| 15 w/w % | 2.06 | 0.051 | 0.246 | 0.150 |

What is claimed is:

1. A method for the treatment of Niemann Pick disease, which comprises administering an effective amount of a S-(carboxyalkyl)thio-cyclodextrin or a pharmaceutically applicable salt thereof to a patient in need thereof.

2. The method of claim 1, wherein the S-(carboxyalkyl)thio-cyclodextrin or a pharmaceutically applicable salt thereof is 6A,6B,6C,6D,6E,7F-Hexakis-S-(2-carboxyethyl)-6A,6B,6C,6D,6E,6F-hexathio-alpha-cyclodextrin or a pharmaceutically applicable salt thereof.

3. The method of claim 1, wherein the S-(carboxyalkyl)thio-cyclodextrin or a pharmaceutically applicable salt thereof is 6A,6B,6C,6D,6E,7F,6G-Heptakis-S-(2-carboxyethyl)-6A,6B,6C,6D,6E,6F,6G-heptathio-beta-cyclodextrin or a pharmaceutically applicable salt thereof.

4. The method of claim 1, wherein the S-(carboxyalkyl)thio-cyclodextrin or a pharmaceutically applicable salt thereof is 6A,6B,6C,6D,6E,7F,6G,6H-Octakis-S-(2-carboxyethyl)-6A, 6B,6C,6D,6E,6F,6G,6H-octathio-gamma-cyclodextrin or a pharmaceutically applicable salt.

* * * * *